United States Patent
Schwartz et al.

(10) Patent No.: US 7,580,755 B1
(45) Date of Patent: Aug. 25, 2009

(54) AUTOMATIC DATA TRANSMISSION RATE ADJUSTMENT

(75) Inventors: Allan R. Schwartz, Moorpark, CA (US); Leonard Mah, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 566 days.

(21) Appl. No.: 11/282,190

(22) Filed: Nov. 18, 2005

Related U.S. Application Data

(60) Provisional application No. 60/630,093, filed on Nov. 19, 2004, provisional application No. 60/630,094, filed on Nov. 19, 2004.

(51) Int. Cl.
*A61N 1/00* (2006.01)

(52) U.S. Cl. .............. 607/60; 340/539.12; 128/904; 128/903

(58) Field of Classification Search .......... 607/30–32, 607/60
See application file for complete search history.

(56) References Cited

U.S. PATENT DOCUMENTS

| | | | | |
|---|---|---|---|---|
| 5,456,692 A * | 10/1995 | Smith et al. | ............. | 607/31 |
| 6,418,346 B1 | 7/2002 | Nelson et al. | ............. | 607/59 |
| 6,442,432 B2 | 8/2002 | Lee | ............. | 607/59 |
| 6,480,745 B2 | 11/2002 | Nelson et al. | ............. | 607/60 |
| 6,497,655 B1 | 12/2002 | Linberg et al. | ............. | 600/300 |
| 6,564,104 B2 | 5/2003 | Nelson et al. | ............. | 607/60 |
| 6,644,322 B2 | 11/2003 | Webb | ............. | 128/899 |
| 6,648,823 B2 | 11/2003 | Thompson | ............. | 600/300 |
| 6,681,003 B2 | 1/2004 | Linder et al. | ............. | 379/106.02 |
| 6,804,558 B2 | 10/2004 | Haller et al. | ............. | 607/30 |
| 6,889,086 B2 * | 5/2005 | Mass et al. | ............. | 607/60 |
| 7,043,305 B2 * | 5/2006 | KenKnight et al. | ............. | 607/60 |
| 2001/0031997 A1 | 10/2001 | Lee | ............. | 607/59 |
| 2001/0039504 A1 | 11/2001 | Linberg et al. | ............. | 705/3 |
| 2002/0082480 A1 | 6/2002 | Riff et al. | ............. | 600/300 |
| 2002/0082665 A1 | 6/2002 | Haller et al. | ............. | 607/50 |
| 2002/0138155 A1 | 9/2002 | Bristol | ............. | 700/2 |
| 2002/0181680 A1 | 12/2002 | Linder et al. | ............. | 379/106.02 |
| 2002/0198473 A1 | 12/2002 | Kumar et al. | ............. | 600/595 |
| 2003/0028082 A1 | 2/2003 | Thompson | ............. | 600/300 |
| 2003/0032991 A1 * | 2/2003 | Poore | ............. | 607/32 |
| 2003/0041866 A1 | 3/2003 | Linberg et al. | ............. | 128/899 |
| 2006/0161213 A1 | 7/2006 | Patel | | |
| 2006/0161214 A1 | 7/2006 | Patel | | |

FOREIGN PATENT DOCUMENTS

| | | |
|---|---|---|
| EP | 1 310 272 A2 | 5/2003 |
| WO | WO 01/03575 A1 | 1/2001 |
| WO | WO 03/025826 A2 | 3/2003 |
| WO | WO 03/025826 A3 | 3/2003 |

* cited by examiner

*Primary Examiner*—Carl H Layno
*Assistant Examiner*—Brian T Gedeon
(74) *Attorney, Agent, or Firm*—Steven M. Mitchell

(57) ABSTRACT

A method for connecting to a remote unit via a communications medium, determining a data transfer rate of the connection, setting a sampling rate between the remote unit and an implantable medical device at least in part as a function of the determined data transfer rate and receiving real time data from the remote unit via said communications medium.

20 Claims, 8 Drawing Sheets

AUTOMATIC DATA TRANSMISSION RATE ADJUSTMENT

CROSS-REFERENCE TO RELATED APPLICATIONS

This application claims the benefit of U.S. Provisional Application No. 60/630,093 filed Nov. 19, 2004, and U.S. Provisional Application No. 60/630,094 filed Nov. 19, 2004 which are incorporated herein by reference.

This patent application is related to the following co-pending U.S. utility patent applications, which are herein incorporated by reference in their entirety:

"Remote Firmware Upgrade," Ser. No. 11/282,979, filed concurrently herewith.

"Virtual Receiver," Ser. No. 10/966,722, filed concurrently herewith.

FIELD OF THE INVENTION

The present invention relates generally to implantable medical devices (IMDs) and more specifically to remote monitoring of patients fitted with an IMD.

BACKGROUND ART

Telemetry is a technology which allows the remote measurement and reporting of information of interest to a user. Telemetry typically refers to wireless communications (i.e. using a radiofrequency system to implement the data link) but can also refer to data transfer over other media, such as a telephone or computer network or via an optical link. Systems which need instructions and data sent to them in order to operate may also require telecommand which is the counterpart of telemetry.

Telemetry is an enabling technology for large complex systems such as spacecraft boosters, oil rigs and chemical plants because it allows automatic monitoring, alerting, and record-keeping necessary for safe, efficient operations. Space agencies such as NASA, ESA, and other agencies use telemetry and telecommand systems to operate spacecraft and satellites. As in other telecommunications fields, international standards exist for telemetry equipment and software. The European Space Agency (ESA) has defined one such standard. In wildlife study and management, telemetry is used to follow members of endangered species. Such animals are now commonly equipped with instrumentation ranging from simple tags to cameras, GPS packages and transceivers to provide position and other information to the scientists, producers, activists, regulators, or other human agencies.

Telemetry is also used for patients who are at risk of abnormal heart activity. Such patients are outfitted with measuring, recording and transmitting devices. A data log can be useful in diagnosis of the patient's condition by doctors. An alerting function can summon nurses if the patient is suffering from an acute or dangerous condition. Telemetry has a wide range of applications for all implantable medical devices (IMDs) and is particularly useful for implantable cardioverter defibrillators (ICDs). ICDs are considered to be a subset of IMDs.

Once an IMD is implanted, it is important that the patient be monitored periodically by a clinic, physician or a commercial group that specializes in IMD follow-up. Some physicians will prefer that the patient be examined in the office on a regular basis to have the IMD checked. Others will arrange an IMD check to be done via transtelephonic monitoring, with periodic visits in the office or clinic. In many offices, the IMD check will be performed by a nurse or technician who is specially trained in management of pacemakers.

IMDs are usually checked with a special device called a wand. A portion of the wand is simply held over the pacemaker and is able to communicate with the pacemaker. It can obtain information about the function of the pacemaker. It can also change certain functions of the pacemaker to whatever the doctor, nurse, or technician feels is most appropriate. A specialized magnet may also be used during the pacemaker evaluation. If transtelephonic monitoring is part of the follow-up, a wand or specialized magnet will probably be given to the patient to use during the telephone evaluations.

However, on initial connection between the system at the patient's end and the system at the clinician's end, communication impairments can cause low baud rate conditions which prevents the execution of the remote patient follow up session. Under these conditions, the available bandwidth cannot support the amount of data coming from the remote patient. Furthermore, low baud rate conditions may prevent the transmission of real time data.

It can also become quite difficult and in some cases even unfeasible to upgrade the firmware on a transmitter used to remotely transfer patient diagnostic data to a receiver at the physician end. This is because the transmitter has to be either brought in-house or a technician will have to go to the patient with the necessary equipment required to perform the upgrade. These upgrades could be for incorporating feature enhancements or even fixes for potential problems in the transmitter. Delays in upgrading could result in patients not getting access to valuable or critical upgrades on time.

Yet another problem is the physical receiver unit on the physician side used to remotely receive patient diagnostic data. The use of a physical receiver unit limits the ability of the physician to conduct the remote follow-up session to locations where such a receiver is available. Thus in the event the physician is not proximate to a physical receiver unit, a follow-up session with a patient will not be possible.

What is needed is a method to optimize remote patient follow up sessions during low baud rate conditions.

BRIEF SUMMARY OF THE INVENTION

The invention comprises a method to connect to a remote unit via a communications medium, determine a data transfer rate of the connection, set a sampling rate between the remote unit and an implantable medical device at least in part as a function of the determined data transfer rate and receive real time data from the remote unit via the communications medium.

Additional features and advantages of the invention will be set forth in the description which follows, and in part will be apparent from the description, or may be learned by practice of the invention.

It is to be understood that both the foregoing general description and the following detailed description are exemplary and explanatory and are intended to provide further explanation of the invention as claimed. The detailed description is not intended to limit the scope of the claimed invention in any way.

BRIEF DESCRIPTION OF THE FIGURES

The accompanying drawings, which are included to provide a further understanding of the invention and are incorporated in and constitute a part of this specification, illustrate embodiments of the invention and together with the description serve to explain the principles of the invention. In the drawings.

Figure 1:
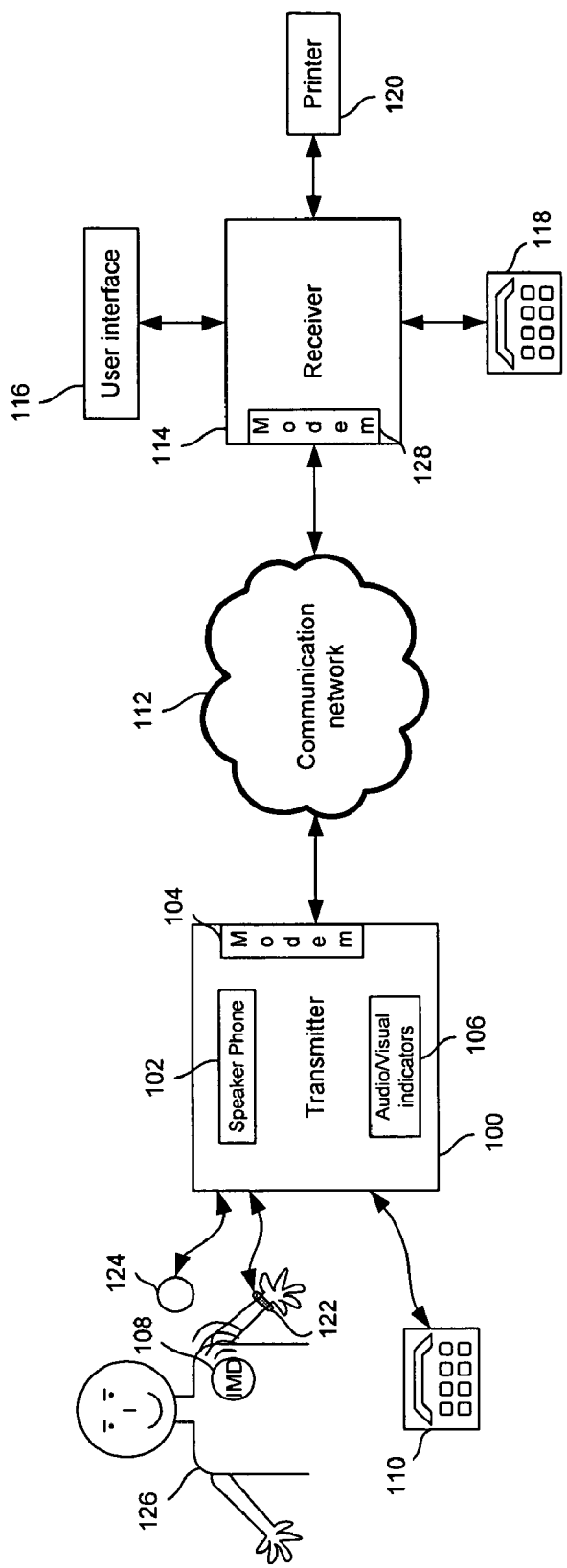
FIG. 1 is a context diagram of a remote monitoring system.

The present invention will now be described with reference to the accompanying drawings. In the drawings, like reference numbers may indicate identical or functionally similar elements. Additionally, the left-most digit(s) of a reference number may identify the drawing in which the reference number first appears.

DETAILED DESCRIPTION OF THE INVENTION

This specification discloses one or more embodiments that incorporate the features of this invention. The embodiment(s) described, and references in the specification to "an example", "one embodiment", "an embodiment", "an example embodiment", etc., indicate that the embodiment(s) or example(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

An IMD is a device that is implanted under the skin of a patient and may be used to obtain patient diagnostic data. An ICD is an IMD that is implanted proximate the heart and under the skin of patients that are at risk of sudden death due to ventricular fibrillation. ICDs typically provide defibrillation if the heart enters a potentially lethal rhythm. The process of implantation of an ICD is similar to implantation of a pacemaker. Similar to pacemakers, these devices typically include a wire that runs through the right chambers of the heart, usually ending in the apex of the right ventricle.

An ICD typically refers to an implantable cardioverter defibrillator or an implantable cardiac device and may also include pacemakers and other implantable cardiac stimulation devices. The term IMD includes ICDs and all other implantable stimulation or diagnostic devices. In one example the IMD is an ICD. In another example it's a pacemaker. In yet another example it is an implanted diagnostic device to monitor, record and transmit patient diagnostic data.

Once an IMD is implanted, a patient may be monitored periodically by an ICD clinic, physician or a commercial group that specializes in IMD follow-up. IMD follow-up is usually done on a defined schedule. Some physicians prefer that the patient be seen in the office on a regular basis to have the IMD checked. Some physicians may arrange an IMD check to be done via transtelephonic monitoring. An IMD is typically checked by a physician or clinician that is specially trained in management of IMDs.

IMDs are typically interrogated with a specialized medical electronic device called a "wand". A portion of the wand is held over the part of a patient's body implanted with an IMD. The wand can then communicate with the IMD. The wand obtains information about the function of the IMD and patient diagnostic data. It may also be used to change certain functions of the IMD to that specified by a physician or clinician. A wand may also be used during the IMD evaluation, and if transtelephonic monitoring is part of the follow-up, a wand will typically be given to the patient to use during the telephone evaluations.

With the use of a remote patient monitoring system, a physician can evaluate a patient with an IMD in real time, even if the two are geographically separated by large distances. These remote monitoring systems make it possible to monitor parameters and settings on an IMD, evaluate real-time electrograms, surface ECGs, delivered therapies, stored electrograms, and clear diagnostics. The complete diagnostics available may be equivalent to a full, in-office wand-based interrogation. These remote monitoring systems allow a medical professional to analyze the transmissions immediately and communicate with the patient in real-time. Calls can be initiated by the patient or follow-up center, and the system can be owned and operated by the office, clinic, or hospital.

Example Environment

FIG. 1 is a context diagram of a remote monitoring system. FIG. 1 shows a transmitter 100 with a built in speaker phone 102, modem 104, audio and visual status indicators 106, a patient 126, an implanted medical device 108, wrist electrodes 122, a wand 124, a transmitter telephone 110, a communication network 112, a receiver 114, an operator interface 116, a receiver phone 118 and a printer 120. The transmitter 100 has a built in speaker phone 102, modem 104, audio and visual status indicators 106 and is coupled to the patient's implanted medical device 108, to wrist electrodes 122, to a transmitter telephone 110 and to a communication network 112. The receiver 114 has a modem 128, a user interface 116 and is coupled to a receiver telephone 118, a printer 120 and to communication network 112.

The wand 124 is wirelessly coupled to the patient's IMD 108 and receives the patient's diagnostic data via telemetry. Wand 124 may be coupled to transmitter 100 wirelessly or by wire. Wand 124 receives patient diagnostic data from IMD 108 and sends it to transmitter 100. IMD 108 typically transfers diagnostic data wirelessly to the transmitter 100. For example the wireless means may be radio frequency transmission. The wrist electrodes 124 may be used to measure the patient's electro cardiogram and other bodily functions. Wrist electrodes 124 may also be coupled to transmitter 100 wirelessly or by wires. Transmitter 100 may send commands to the patient's IMD 108 to either control the IMD 108 or to receive inter-cardial electrogram (IEGM) data from the IMD 108. Transmitter 100 may receive surface ECG data from wrist electrodes 122.

The audio and visual indicators 106 may be used to provide operational status of either one or both transmitter 100 and IMD 108 to the patient 126. For example, transmitter 100 can have a light and/or a series of beeps to indicate whether the wand 124 is in the correct position to read data from the IMD 108. Another light and a different series of beeps may indicate that the patient 126 should activate the speaker phone 102 to communicate with a physician and yet another light and series of beeps may indicate whether there is a problem with transmitter 100, IMD 108 or with the connection to receiver 114. The lights can be of different colors and the beeps can have different tones to indicate different status information. The transmitter 100 enables voice communication with the remotely located physician via the externally attached transmitter phone 110 or the internal speakerphone 102.

The receiver 114 is coupled to a receiver telephone 118, a printer 120 and either has a built in or external user interface 116. The receiver 114 can be implemented on a personal computer using specialized software or may be a custom hardware unit running specialized software. The user interface 116 can be a graphical user interface (GUI) that can be used by the physician to send commands to transmitter 100 and display patient diagnostic data received from transmitter 100. The receiver 114 can also be used to perform upgrades of transmitter 100 firmware via communication medium 112. The receiver phone 118 can be used to contact the patient 126. Receiver 114 is typically used to initiate the remote follow-up procedure with the patient 126 and generate patient data reports. The patient data reports can be printed using the printer 120.

A "follow-up session" typically involves the remote monitoring of patient's diagnostic data. A physician may execute a single session that involves the remote follow-up of a patient's IMD 108. The physician is able to "interrogate" the IMD 108 which typically involves using receiver 114 to connect to transmitter 100 and receive real time and/or stored data collected by transmitter 100 from IMD 108. The physician can view the interrogation data received from transmitter 100 via user interface 116, and print a follow-up session report via printer 120. The physician can perform both "standard" and "custom" follow-ups. A standard follow up may be a set of pre-programmed data requests made by receiver 114 to transmitter 100. A custom follow-up may allow the physician to customize the data requests made to transmitter 100 via receiver 114.

The follow-up session to remotely monitor a patient's IMD 108 and receive other diagnostic and biometric data typically involves the physician calling the patient's transmitter unit. The patient 126 communicates with the physician via the speakerphone 102 on transmitter 100 or the transmitter telephone 110 and positions the wand 124 and wrist electrodes 122 to enable transfer of diagnostic data. The audio and visual indicators 106 on transmitter 100 indicate if the wand 124 and wrist electrodes 122 are in position to enable data collection. If the communication network 112 can only transmit voice or data at a given time then the patient 126 may hang up the phone line so that data can be transmitted to the physician from transmitter 100 via communication network 112. If the communication network is a VoIP network that can support simultaneous transmission of voice and data, then the patient 126 can continue to communicate with a physician on the transmitter phone 110 while the data is being transmitted to receiver 114. Since the system is capable of transmitting real time patient diagnostic data, the physician can immediately analyze the received data and provide the necessary advice to patient 126 via transmitter telephone 110 and/or audio and visual indicators 106. The system can support the simultaneous transmission of stored data as well as real time data from transmitter 100 to receiver 114.

The system shown in FIG. 1 supports multiple remote patient follow-up functions including but not limited to the interrogation of programmed parameters and diagnostics from IMD 108, acquisition of real-time endocardial EGM, surface ECG obtained from wrist electrodes 122, and real-time patient data measurements. The system in FIG. 1 also supports diagnostic operations including but not limited to clearing diagnostics, clearing EGM data, updating and adding of trending points such as battery voltage, pacing lead impedance, and signal amplitude. The system in FIG. 1 is also capable of disabling all features of the wand 124 software that involve modification of operating parameters or high risk diagnostic follow-up tests that require the presence of clinical personnel, including but not limited to the programming of IMD 108 timing, output, sensing, therapy and diagnostic parameters, capture testing, device based testing, non-invasive programmed stimulation (NIPS), Direct Current (DC) fibber, burst fibber, and shock-on-T Fibber, wand commanded shock, high voltage lead integrity check, temporary pacing and capacitor maintenance.

The system shown in FIG. 1 may also support acquiring a continuous stream of real-time surface and intracardial ECG data for display on user interface 116 and printing surface and intracardial ECGs via printer 120. The system may also collect surface and endocardial electrograms with a delay of not more than 3 seconds between the surface event and the display of the data on user interface 116. The system allows the display of pacing spike enhancements on surface ECGs. The pacing spike enhancements may be configured to be on or off depending on user requirements. The pacing spike enhancement marker is typically within ±20 ms of the pacing marker that triggered it. The system may perform an initial interrogation in less than 3 minutes. An initial interrogation may include interrogation of all applicable parameters and any available diagnostics, including the stored EGM directory. The receiver 114 may also be able to retrieve n minutes of stored EGM data from transmitter 100 in less than n minutes. The receiver 114 can support the interrogation of multiple devices while in the same session.

Remote Adjustment of Data Rate

The data connection between the receiver 114 and transmitter 100 is negotiated by their respective modems 128 and 104. After the data rate or baud rate has been negotiated, receiver 114 and/or transmitter 100 can interrogate either of modems 128, 104 to determine the baud rate of the connection. However, on initial connection between the transmitter 100 at the patient's end and the receiver 114 at the clinician's end, communication impairments can cause low baud rate conditions which may prevent the execution of the remote patient follow up session. Under these conditions, the available bandwidth on communication network 112, may not be able to support the amount of real time data coming from the remote patient. To enable a remote follow up session to continue in low baud rate connections the transmitter 100 may need to reduce the amount of data being transmitted. The present invention optimizes the amount of data that can be transmitted at a given data rate connection.

An embodiment of the invention optimizes the amount of data transmitted at a given data rate or available bandwidth. In one example the available bandwidth is optimized by lowering the sampling rate for selected measurements. This reduces the number of characters per packet of data transmitted by transmitter 100. Another example selects only certain data types for transmission by transmitter 100. By selecting data types for transmission or any combination of reducing the sampling rate for certain data types and selecting certain data types for transmission, more information can be transmitted at lower baud rates. In another example, multiple data packets may be combined to reduce the overall packet overhead thereby increasing the amount of patient diagnostic data transmitted. Combining data packets may be coupled with one or more of reducing the sampling rate and selecting certain data types for transmission.

Figure 2:
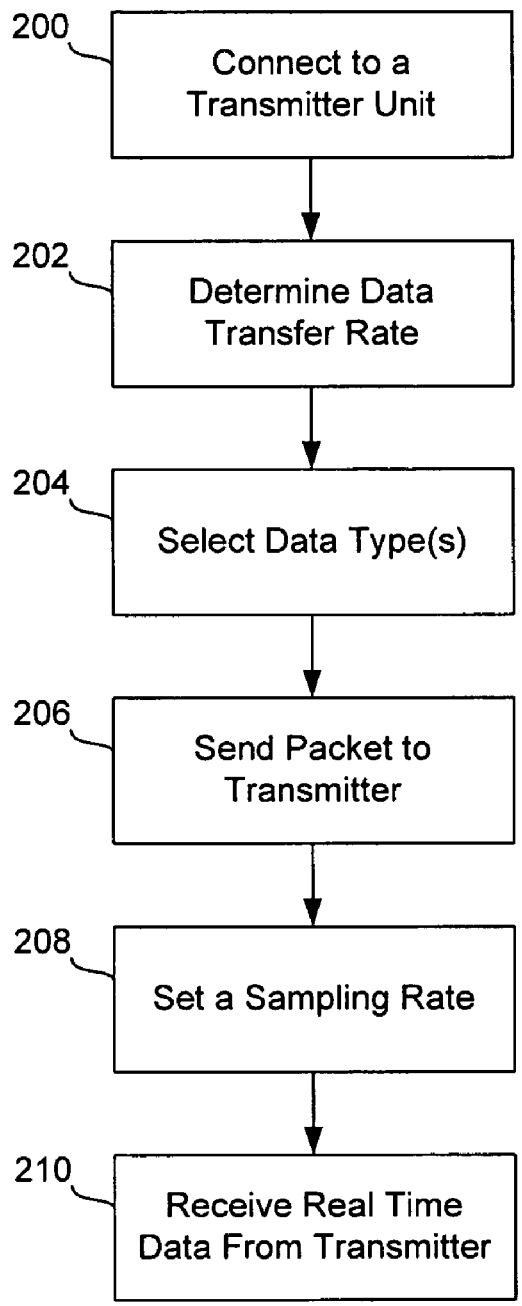
FIG. 2 is an example flowchart of steps that may be performed by a receiver to remotely adjust characteristics of data transmitted by a transmitter as a function of a determined data transfer rate.

FIG. 2 is an example flowchart of steps that may be performed by receiver 114 to remotely adjust data transmitted by transmitter 100 as a function of a determined data transfer rate. These steps may be performed by receiver 114 hardware, software, firmware or any combination thereof.

In step 200, the receiver 114 connects to the transmitter 100. The receiver modem 128 typically connects to the transmitter modem 104 via communication network 112.

Next, in step 202, the receiver 114 determines the data transfer rate of the connection between the receiver 114 and the transmitter 100. The data connection between the receiver 114 and transmitter 100 is negotiated by their respective modems 104, 128. The receiver 114 typically obtains the data transfer rate between the receiver 114 and the transmitter 100 from modem 128.

In step 204, the receiver 114 determines the data types that can be received from transmitter 100 based on the data transfer rate determined in step 202. For example only data types that can be accommodated by the data transfer rate determined in step 202 may be selected. For low data transfer rates, data types that require fewer characters per packet (such as data types that use a low sampling rate) may be selected whereas for high data transfer rates, data types that require more characters per packet (such as data types that use a high sampling rate) may be selected. In yet another example, data types sent in two or more packets may be combined into a single packet to reduce overhead. Examples of data type selection and combination of packets based on data transfer rates are described below.

In step 206, the receiver 114 may send a signal or a packet to the transmitter 100 instructing transmitter 100 to transmit only data types selected in step 204. In another example, the receiver 114 may send a signal or a packet instructing the transmitter 100 to combine data in two or more packets to reduce overhead.

In optional step 208, the receiver 114 may send a signal or a packet instructing transmitter 100 to sample data from IMD 108 or wrist electrodes 122 at a given sampling rate. Based on the sampling rate received from receiver 114, the transmitter 100 may alter the real time rate at which data is sampled from IMD 108 via wand 124. In one example, based on the data type(s) received from receiver 114 in step 206 and the data transfer rate determined in step 202, the transmitter 100 may alter the sampling rate at which data is sampled from IMD 108 via wand 124. Examples of sampling rate selection based on data transfer rates are described below.

In step 210, the receiver 114 receives real time data from transmitter 100. Transmitter 100 obtains real time data by interrogating IMD 108 via wand 124 and via wrist electrodes 122. In another example, data stored previously in transmitter 100 may also be sent along with the real time data. In yet another example, only stored data may be sent. The stored data may also be down-sampled or up-sampled to reduce data size and optimize use of the available data rate determined in step 202.

Figure 3:
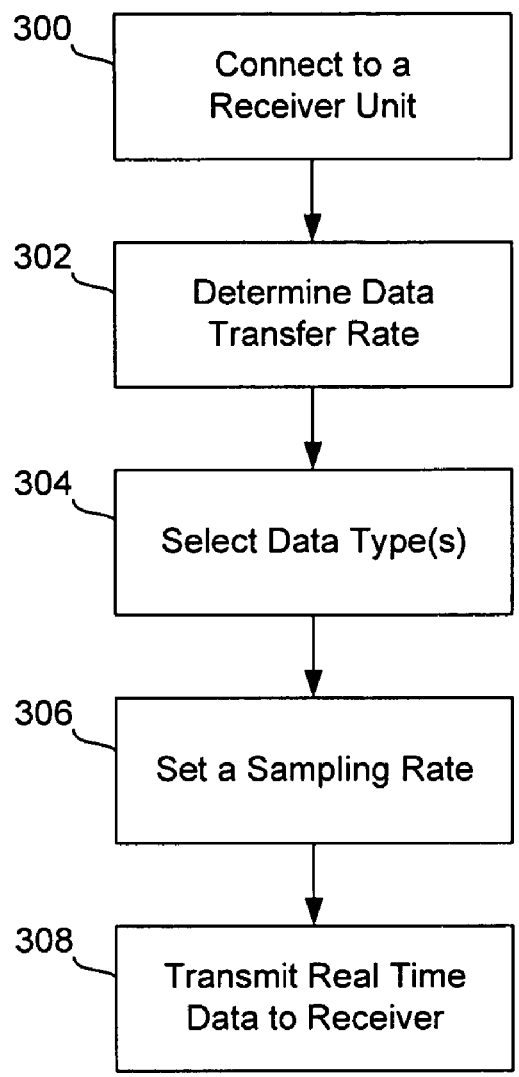
FIG. 3 is an example flowchart of steps that may be performed by a transmitter to adjust characteristics of data transmitted to a receiver as a function of a determined data transfer rate.

In another example, transmitter 100 may connect to receiver 114 and upload real time data as a function of the determined data rate. FIG. 3 is an example flowchart of steps that may be performed by transmitter 100 to adjust data transmitted to a receiver 114 as a function of a determined data transfer rate. These steps may be performed by transmitter 100 hardware, software, firmware or any combination thereof.

In step 300, the transmitter 100 connects to the receiver 114. The transmitter modem 104 typically connects to the receiver modem 128 through communication network 112.

Next, in step 302, the transmitter 100 determines the data transfer rate of the connection between the receiver 114 and the transmitter 100. The data connection between the receiver 114 and transmitter 100 is typically negotiated by their respective modems 128, 104. The transmitter 100 typically obtains the data transfer rate between the receiver 114 and the transmitter 100 from modem 104.

In step 304, transmitter 100 selects the data types that can be transmitted to receiver 114 based on the data transfer rate determined in step 302. For example only data types that can be accommodated by the data transfer rate determined in step 302 may be selected. For low data transfer rates, data types that require fewer characters per packet (such as data types that use a low sampling rate) may be selected whereas for high data transfer rates, data types that require more characters per packet (such as data types that use a high sampling rate) may be selected. In yet another example, data types sent in two or more packets may be combined into a single packet to reduce overhead. Examples of data type selection and combination of packets based on data transfer rates are described below.

In optional step 306, transmitter 100 may set a sampling rate at which wand 124 samples data from IMD 108 and/or wrist electrodes 122. In one example the sampling rate may be a function of the data types determined in step 304 and in another example the sampling rate may be independent of the data types determined in step 304 and based solely on the data transfer rate determined in step 302. Examples of selecting sampling rates are described below.

In step 308, real time data obtained by interrogating IMD 108 and from wrist electrodes 122 is transmitted to the receiver 114 by transmitter 100. In another example, data stored previously in transmitter 100 may be sent along with real time data. In yet another example, only stored data may be transmitted. The stored data may be down-sampled or up-sampled by transmitter 100 to reduce data size and optimize use of the available data rate determined in step 302.

Alternate Embodiments of Remote Data Rate Adjustment

Surface ECG data sampled at 512 Hz may require 10 characters per packet whereas surface ECG data sampled at 256 Hz may require only 7 characters per packet. EGM data with markers may require 8 characters per packet whereas EGM data without markers may require only 3 characters per packet. Table 1 shows examples of different types of real time data and the number of characters per packet needed to transmit them.

TABLE 1

Examples of real time data types.

| Real Time Data Type | Characters per Packet |
|---|---|
| Surface ECG at 512 Hz sampling | 10 |
| Surface ECG at 256 Hz sampling | 7 |
| EGM with marker data | 8 |
| EGM without marker data | 3 |
| Block Reading Data | 8 |

The time required to transmit each character (CharTime), assuming each character to have 10 bits per byte, in milliseconds is given by:

$$CharTime(ms) = \left[\frac{10 \text{ bits-per-byte}}{BaudRate}\right] \times 1000 \quad \text{equation 1}$$

where BaudRate is in bits/second and is given as:

$$BaudRate \text{ (bits/sec)} = \left[\frac{10 \text{ bits-per-byte}}{CharTime \text{ (ms)}}\right] \times 1000 \quad \text{equation 2}$$

The time to send 11 bytes of data per packet (PT) is given by:

$$PT(ms) = 11 \text{ bytes} \times CharTime \quad \text{equation 3}$$

If the baud rate at which the connection is taking place is below the sum of the minimum baud rates for each data type, then only some of the data types may be selected for reception or transmission as in steps 204 and 304. For example, to transmit surface ECG data sampled at 512 Hz, the baud rate using equation 2 and data from table 1 is given by:

$$BaudRate \text{ for } ECG \text{ at } 512 \text{ Hz} = \frac{10 \times 10}{7.18 \text{ ms}} = 12{,}804 \text{ baud} \quad \text{equation 4}$$

To transmit surface ECG data sampled at 256 Hz, the baud rate using equation 2 and data from table 1 is given by:

$$BaudRate \text{ for } ECG \text{ at } 256 \text{ Hz} = \frac{10 \times 7}{7.81 \text{ ms}} = 8{,}962 \text{ baud} \quad \text{equation 5}$$

If the data connection rate determined in steps 202 and 302 is 10,000 baud, then it may not be possible to transmit real time surface ECG data sampled at 512 Hz since that requires 12,804 baud as determined in equation 4. In this case, ECG data sampled at 256 Hz may be transmitted since it requires 8,962 baud as determined in equation 5. The selection of data types for transmission is determined in steps 204 and 304. Based on the number of characters defined for each packet in Table 1, the baud rate for other data types such as EGM with or without marker data and block reading data may also be calculated. In the examples presented throughout, we assume that the time for transmitting one frame is 7.81 ms. This time is used for example purposes only and does not limit the invention in any way.

The limiting factor in data transmission or reception may be the telemetry speed. For example, at a baud rate of 14,085, the time to send a packet may equal the time it takes to read a telemetry frame. If the baud rate is greater than 14,085, then, the time it takes to send a packet of read data is less than the time it takes to send and read the telemetry frame. In this example, for baud rates greater than 14,085, the limiting factor is the telemetry speed. At lower baud rates fewer characters can be transmitted per millisecond and hence fewer data elements can be transmitted. By using the steps in the flowcharts in FIGS. 2 and 3 and in examples presented herein, at lower baud rates, more data elements may be transmitted. Table 2 below shows examples of the number of characters and the types of real time data (based on the number of characters required per data type from table 1) that can be transmitted per 7.81 millisecond at different baud rates.

TABLE 2

Examples of number of characters and data types transmitted at different baud rates.

| Baud Rate | Characters per 7.81 ms | Allowable Data Combinations |
|---|---|---|
| 24000 | 18 | All types of data |
| 21600 | 16 | Surface ECG sampled at 256 Hz, EGM data, and Marker/Data (15 chars) |
| | | Surface ECG sampled at 256 Hz and Block Reading Data (15 chars) |
| 19200 | 14 | Surface ECG sampled at 256 Hz, EGM with no marker data (10 chars) |
| | | Block Reading Data (8 chars) |
| 16800 | 13 | Surface ECG sampled at 256 Hz and EGM with no marker data (10 chars) |
| | | Block Reading Data (8 chars) |
| 14400 | 11 | Surface ECG sampled at 256 Hz and EGM with no marker data (10 chars) |
| | | Block Reading Data (8 chars) |

As in steps 204 and 304, ECG, EGM and marker data may be selected to be transmitted or received in one packet instead of two. As a result the overhead bytes associated with each packet are reduced and more data can be sent at lower baud rates. For example if 4 samples of surface ECG data and 2 frames of EGM and marker data can be sent in one packet instead of two, then the overhead will be averaged over 2 frames and more data can be sent at lower baud rates. In another example, overhead data such as the "packet type" byte, which identifies the type of packet being transmitted, the "sequence number" and the "cyclic redundancy code" (CRC) might require 4 bytes of data and have to be appended to each packet being transmitted. For example, if a packet is transmitted every 15.62 ms then the average overhead is 2 bytes thereby reducing the size of the transmitted packet. Table 3 shows an example of the number of bytes needed for example data types in a packet of real time data sent every 15.62 ms.

TABLE 3

Examples of the number of bytes for different data types sampled at 512 Hz in a packet sent every 15.62 ms.
All Real Time Data in One Packet send every 15.62 ms - 512 Hz sampling

| Real Time Packet Item | Bytes needed |
|---|---|
| Packet type byte | 1 |
| Surface ECG samples 1&2 (512 Hz sampling) | 3 |
| Surface ECG samples 3&4 (512 Hz sampling) | 3 |
| Surface ECG samples 5&6 (512 Hz sampling) | 3 |
| Surface ECG samples 7&8 (512 Hz sampling) | 3 |
| EGM 1&2 | 2 |
| Marker 1 | 4 |
| EGM 3&4 | 2 |
| Marker 2 | 4 |
| Sequence Number | 1 |
| CRC | 2 |

The packet shown in table 3 sends 28 total bytes per 15.62 ms or an average of 14 bytes per 7.81 ms instead of 16 bytes per 7.81 ms as would be the case if two packets, each having their own overhead were transmitted individually.

In another example, as in steps 208 and 306, in addition to the above optimizations, if the sampling rate of the surface ECG is changed from 512 Hz to 256 Hz, then the number of bytes transmitted per 15.62 milliseconds is reduced. Table 4 below illustrates examples of the number of bytes for different data types sampled at 256 Hz in a packet sent every 15.62 ms.

TABLE 4

Examples of the number of bytes for different data types sampled at 256 Hz in a packet sent every 15.62 ms
All Real Time Data in One Packet send every 15.62 ms - 256 Hz sampling

| Real Time Packet Item | Bytes needed |
|---|---|
| Packet type byte | 1 |
| Surface ECG samples 1&2 (256 Hz sampling) | 3 |
| Surface ECG samples 3&4 (256 Hz sampling) | 3 |
| EGM 1&2 | 2 |
| Marker 1 | 4 |
| EGM 3&4 | 2 |
| Marker 2 | 4 |
| Sequence Number | 1 |
| CRC | 2 |

The packet shown in table 4 has 22 total bytes per 15.62 ms or an average of 11 bytes per 7.81 ms instead of 13 bytes per 7.81 ms as would be the case if two packets, each having their own overhead were transmitted individually. Also, the number of bytes when using 256 Hz sampling as in table 4 is less than the number of bytes when using 512 Hz sampling as in table 3. Thus, by reducing the average overhead per packet of transmitted data, the sampling rate and or by selecting transmission data types, data can be transmission is possible and can be optimized for low baud rate conditions. Table 5 below shows another example of optimizing data transfer by reducing overhead by combining packets.

TABLE 5

Examples of optimizing data transfer at different baud rates by reducing overhead per packet.
Data transfer with reduced overhead per packet

| Baud Rate | Characters per 7.81 ms | Allowable Data Combinations |
|---|---|---|
| 24000 | 18 | Any |
| 21600 | 16 | Any |
| 19200 | 14 | Surface ECG at 512 Hz sampling and EGM with marker data (14 chars) OR Block Reading Data (8 chars) |
| 16800 | 13 | Surface ECG at 256 Hz sampling and EGM with marker data (11 chars) OR Block Reading Data (8 chars) |
| 14400 | 11 | Surface ECG at 256 Hz sampling, EGM with marker data (11 chars) OR Block Reading Data (8 chars) |

In another example, as in steps 208 and 306, if the ECG sampling rate is changed to 128 Hz, then the packet size is reduced further. With a reduced ECG packet size more data and more combinations of different data types may be transmitted at lower baud rates without the need to combine packets and reduce overhead per packet. This modification of the sampling rate allows the reception of all real time data at a baud rate of 19,200 as compared to 21,600 with no changes in packet format. In addition, the 19,200 baud rate also allows reception of surface ECG data with block reading. Table 6 is an example of data combinations that can be transmitted at different baud rates when the ECG sampling rate has been modified to 128 Hz.

TABLE 6

Example of optimizing data transfer at different baud rates using 128 Hz sampling.
Data transfer with reduced sampling rate of 128 Hz

| Minimum Baud Rate | Characters per 7.81 ms | Allowable Data Combinations |
|---|---|---|
| 24000 | 18 | Any |
| 21600 | 16 | Surface ECG at 256 Hz sampling and EGM with marker data (15 chars) OR Surface ECG at 256 Hz sampling and Block Reading Data (15 chars) |
| 19200 | 14 | Surface ECG at 128 Hz sampling and EGM with marker data (14 chars) OR Surface ECG at 128 Hz sampling and Block Reading Data (14 chars) |
| 16800 | 13 | Surface ECG at 256 Hz sampling and EGM with no marker data (10 chars) OR Block Reading Data (8 chars) |
| 14400 | 11 | Surface ECG at 256 Hz sampling and EGM with no marker data (10 chars) OR Block Reading Data (8 chars) |

In another example, a surface ECG sampling rate of 128 Hz in combination with a reduced overhead per packet may allow transmission of greater amounts of real time data at reduced baud rates. In yet another example, if all the real time data is incorporated in one packet, then a 256 Hz surface ECG in combination with EGM data and marker data can be transmitted at 14,400 baud. In a further example, all real time data can be transmitted without reducing the sampling rate by compressing or encoding the data instead of reducing the sampling rate or overhead per packet. In another example, all real time data can be transmitted by encoding some features and reducing the sampling rate for other features. In yet another example, disabling certain real time features will allow transmission of other real time features. In one example, there is a table of frame types that lists the type of data that can be sent at a particular baud rate. This table can be either at the transmitter end or the receiver end or at both ends. The transmitter 100 or receiver 114 looks up the frame type to determine the type of real time data to transmit or receive.

Remote Upgrade of Firmware

It can become quite difficult and in some cases even unfeasible to upgrade the firmware on transmitter 100 used in the remote follow-up of patients fitted with an IMD 108. This is because the transmitter 100 has to be either brought in-house or a technician will have to go to the patient with the necessary equipment required to perform the upgrade. These upgrades could be for incorporating feature enhancements or even fixes for potential problems in transmitter 100. Delays in upgrading could result in patients not getting access to valuable or critical upgrades on time. If the patient is traveling it becomes even more challenging to perform the upgrade. It is inconvenient and expensive for the patient to bring the transmitter 100 to either a clinic or a factory outlet for an upgrade. A firmware upgrade may be performed remotely via the internet, trans-telephonically or by any other communications means in communication network 112 to mitigate this problem.

An example provides for a remote upgrade of transmitter 100 firmware. In one example a system is provided where such an upgrade can be accomplished from anywhere in the world via the internet or trans-telephonically. Communication media such as, for example, in communications network 112 can be used to perform the upgrade from a remote location. Such upgrades can be performed at the convenience of the patient. Furthermore, if there is a break in communication during an upgrade or if the upgrade cannot be performed successfully the transmitter 100 can still be made functional by using the previous version of firmware.

Figure 4:
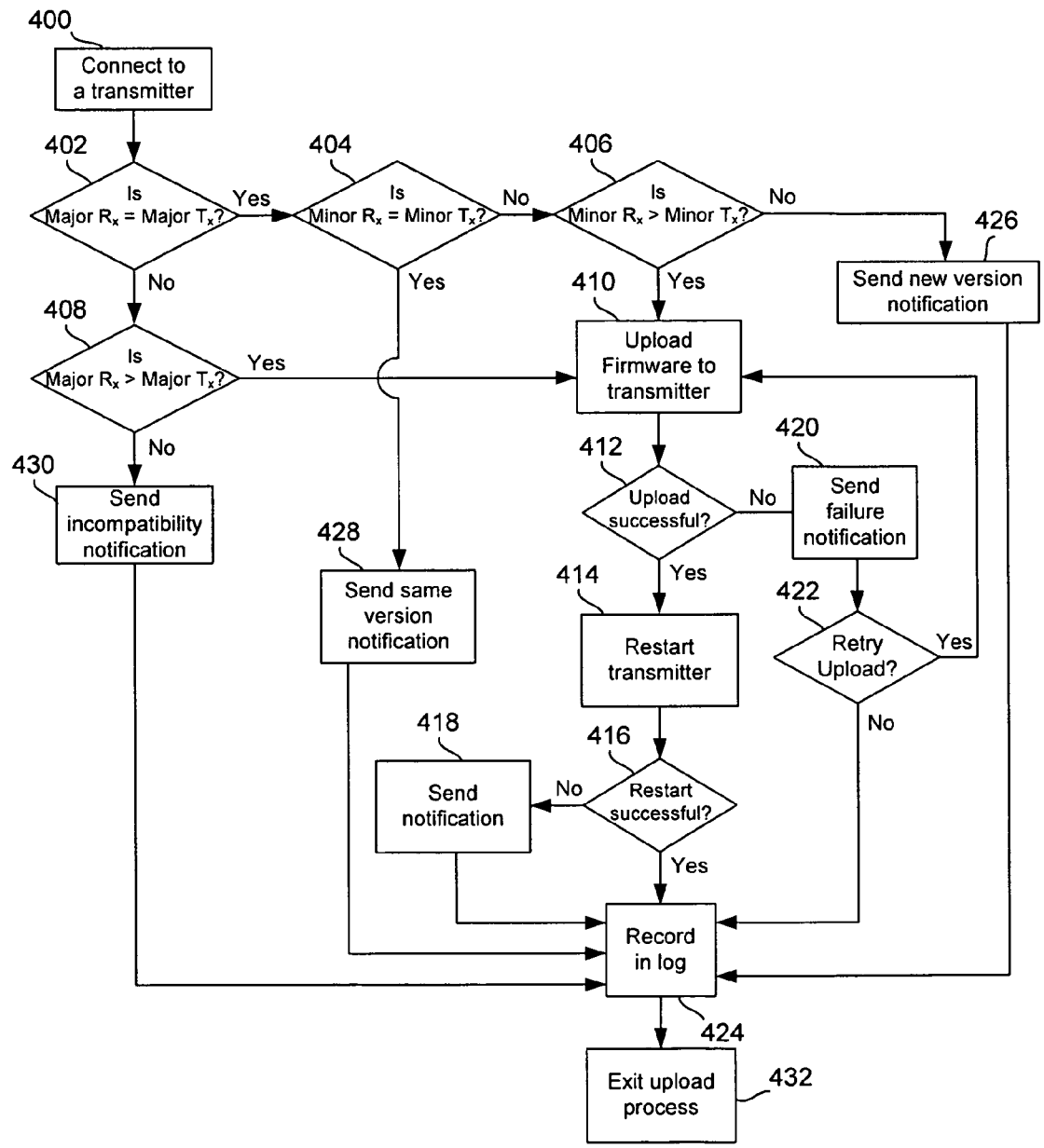
FIG. 4 is an example flowchart of steps that may be performed by a receiver to remotely upgrade transmitter firmware.

FIG. 4 is an example flowchart of steps that may be performed by a receiver 114 to remotely upgrade transmitter 100 firmware. These steps may be performed by receiver 114 hardware, software, firmware or any combination thereof. In the flowchart shown in FIG. 4, $R_x$ is the firmware revision number stored in receiver 114 and $T_x$ is the firmware revision number loaded in transmitter 100. The firmware revision numbers $R_x$ and $T_x$ of both the receiver 114 and the transmitter 100 are in an "a.b" format, where "a" denotes the major firmware revision number and "b" denotes the minor firmware revision number. For example, a firmware revision number may be 23.04. In this example, the major firmware revision number is "23" and the minor firmware revision number is "04". In the flowchart in FIG. 4, "Major $R_x$" refers to the "a" portion of $R_x$ and "Minor $R_x$" refers to the "b" portion of $R_x$. Similarly, the "Major $T_x$" refers to the "a" portion of $T_x$ and the "Minor $T_x$" refers to the "b" portion of $T_x$.

In step 400, the receiver 114 connects to the transmitter 100. The receiver 114 modem 128 typically connects to the transmitter 100 modem 104 via communication network 112.

Next, in step 402, the receiver 114 determines if the major $R_x$ is equal to the major $T_x$.

If the major $R_x$ is determined to not be equal to the major $T_x$ in step 402, then in step 408, the receiver 114 determines if the major $R_x$ is greater than the major $T_x$.

If the major $R_x$ is determined to be greater than the major $T_x$ in step 408, then in step 410, the receiver 114 uploads the new firmware to the transmitter 100.

If the major $R_x$ is determined to be equal to the major $T_x$ in step 402, then in step 404, the receiver 114 determines whether the minor $R_x$ is equal to the minor $T_x$.

If the minor $R_x$ is determined to not be equal to the minor $T_x$ in step 404, then in step 406, the receiver 114 determines whether the minor $R_x$ is greater than the minor $T_x$.

If the minor $R_x$ is determined to be greater that the minor $T_x$ in step 406, then in step 410, the receiver 114 uploads the new firmware to the transmitter 100.

In step 412, the receiver 114 determines if the firmware upload to transmitter 100 was successful.

If the firmware upload to transmitter 100 was determined to be successful in step 412, then in step 414, the receiver 114 signals the transmitter 100 to restart.

In step 416, the receiver 114 determines if the transmitter 100 restarted correctly. The receiver 114 may accomplish this by sending a test signal to transmitter 100 or by waiting to receive a response from transmitter 100 on successful startup.

If it was determined that the transmitter 100 restarted successfully in step 416, then in step 424, the receiver 114 records a log of transactions with transmitter 100 in one or both receiver 114 and transmitter 100 and exits the upload process in step 432.

If transmitter 100 restart is determined to be unsuccessful in step 416, then in step 418, the receiver 114 may notify a user at receiver 114 end and/or the user at transmitter 100 end. In one example, receiver 114 may send restart failure notification via telephone 110 and/or audio visual indicators 106 to the user at transmitter 100 end. In another example receiver 114 may send restart failure notification to the clinician at receiver 114 end via telephone 118, user interface 116 and/or printer 120. The receiver 114 then records a log of transactions with transmitter 100 in one or both receiver 114 and transmitter 100 in step 424 and exits the upload process in step 432.

If it is determined that the upload to transmitter 100 was unsuccessful in step 412, then in step 420, the receiver 114 may send upload failure notification to users at one or both receiver 114 and transmitter 100 ends. The notification may be sent by methods similar to those described in step 418.

In step 422, the receiver 114 may query users at one or both the receiver 114 and transmitter 100 ends to retry uploading firmware to transmitter 100. The user on the receiver 114 end may be queried via interface 116 or by an automated message using receiver telephone 118. The user on the transmitter 100 end may be queried via an automated message using transmitter telephone 110.

If the query in step 422 results in an instruction to retry uploading firmware to transmitter 100, then the receiver 114 returns to step 410 and again tries to upload firmware to transmitter 100, otherwise the receiver 114 proceeds to step 424 and records a log of transactions with transmitter 100 in one or both receiver 114 and transmitter 100 and exits the upload process in step 432.

If it is determined that the minor $T_x$ is greater than the minor $R_x$ in step 406, then in step 426, the receiver 114 may send notification that a newer version of firmware exists than that available on receiver 114 to users at one or both receiver 114 and transmitter 100 ends. The notification may be sent by methods similar to those described in step 418. The receiver 114 then records a log of transactions with transmitter 100 in one or both receiver 114 and transmitter 100 in step 424 and exits the upload process in step 432.

If it is determined in step 404 that the minor $R_x$ is equal to the minor $T_x$, then in step 428, the receiver 114 may notify users at one or both the receiver 114 and transmitter 100 ends that transmitter 100 has the same version of firmware as stored in receiver 114. The notification may be sent by methods similar to those described in step 418. The receiver 114 then records a log of results from transactions with transmitter 100 in one or both receiver 114 and transmitter 100 in step 424 and exits the upload process in step 432.

If it is determined in step 408 that the major $R_x$ is less than the major $T_x$, then in step 430, the receiver 114 may notify users at one or both the receiver 114 and transmitter 100 ends that the firmware stored in receiver 114 may possibly be incompatible with the firmware version loaded in transmitter 100. The notification may be sent by methods similar to those described in step 418. The receiver 114 then records a log of transactions with transmitter 100 in one or both receiver 114 and transmitter 100 in step 424 and exits the upload process in step 432.

Figure 5:
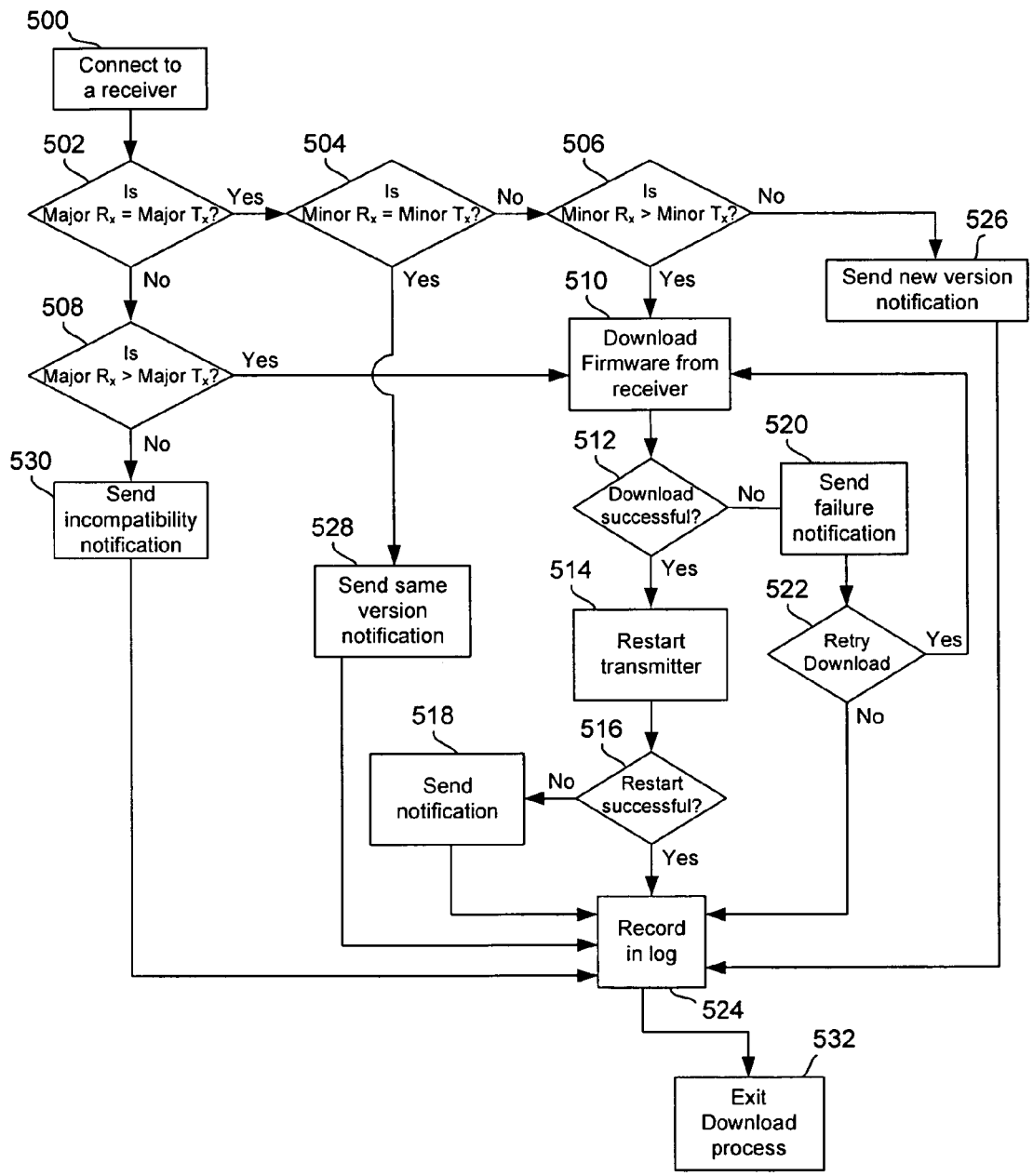
FIG. 5 is an exemplary flowchart of steps that may be performed by a transmitter to upgrade its firmware.

FIG. 5 is an exemplary flowchart of steps that may be performed by transmitter 100 to upgrade its firmware. These steps may be performed by transmitter 100 hardware, software, firmware or any combination thereof. In the flowchart in FIG. 5, $R_x$ is the firmware revision number stored in receiver 114 and $T_x$ is the firmware revision number loaded in transmitter 100. The firmware revision numbers $R_x$ and $T_x$ of both the receiver 114 and the transmitter 100 are in an "a.b"

format, where "a" denotes the major firmware revision number and "b" denotes the minor firmware revision number. For example, a firmware revision number may be 23.04. In this case the major firmware revision number is 23 and the minor firmware revision number is 04. In the flowchart in FIG. 5, "Major $R_x$" is the "a" portion of $R_x$ and "Minor $R_x$" is the "b" portion of $R_x$. The "Major $T_x$" refers to the "a" portion of $T_x$ and the "Minor $T_x$" refers to the "b" portion of $T_x$.

In step 500, the transmitter 100 connects to the receiver 114. The transmitter 100 modem 104 typically connects to the receiver modem 128 via communication network 112.

Next, in step 502, the transmitter 100 determines if the major $R_x$ is equal to the major $T_x$.

If the major $R_x$ is determined to not be equal to the major $T_x$ in step 502, then in step 508, the transmitter 100 determines if the major $R_x$ is greater than the major $T_x$.

If the major $R_x$ is determined to be greater than the major $T_x$ in step 508, then in step 510, the transmitter 100 downloads the new firmware from receiver 114.

If the major $R_x$ is determined to be equal to the major $T_x$ in step 502, then in step 504, the transmitter 100 determines whether the minor $R_x$ is equal to the minor $T_x$.

If the minor $R_x$ is determined to not be equal to the minor $T_x$ in step 504, then in step 506, the transmitter 100 determines whether the minor $R_x$ is greater than the minor $T_x$.

If the minor $R_x$ is determined to be greater that the minor $T_x$ in step 506, then in step 510, the transmitter 100 downloads the new firmware from receiver 114.

In step 512, the transmitter 100 determines if the firmware download from receiver 114 was successful.

If the firmware download from receiver 114 was determined to be successful in step 512, then in step 514, the transmitter 100 attempts to restart itself.

In step 516, the transmitter 100 determines if the restart is successful. The transmitter 100 may accomplish this by using software or firmware similar to Microsoft Windows™ "safe mode" operation.

If it was determined that the transmitter 100 restarted successfully in step 516, then in step 524, transmitter 100 records a log of transactions with receiver 114 in one or both receiver 114 and transmitter 100 and exits the download process in step 532.

If transmitter 100 restart is determined to be unsuccessful in step 516, then, in step 518, the transmitter 100 may notify a user at receiver 114 end and/or a user at transmitter 100 end. In one example, transmitter 100 may send restart failure notification via telephone 110 and/or audio and visual indicators 106 to the user at transmitter 100 end. In another example transmitter 100 may send restart failure notification to a user at receiver 114 end via telephone 118, user interface 116 and/or printer 120. The transmitter 100 then records a log of transactions with receiver 114 in one or both receiver 114 and transmitter 100 in step 524 and exits the upload process in step 532.

If it is determined that the download from receiver 114 was unsuccessful in step 512, then in step 520, the transmitter 100 may send upload failure notification to users at one or both receiver 114 and transmitter 100 ends. The notification may be sent by methods similar to those described in step 518.

In step 522, the transmitter 100 may query users at one or both the receiver 114 and transmitter 100 ends to retry downloading firmware from receiver 114. The user on the receiver 114 end may be queried via interface 116 or receiver telephone 118. The user on the transmitter 100 end may be queried via transmitter telephone 110 or audio/visual indicators 106.

If the query in step 522 results in an instruction to retry downloading firmware from receiver 114, then in step 510, the transmitter 100 returns to step 510, otherwise transmitter 100 proceeds to step 524 and records a log of transactions with receiver 114 in one or both receiver 114 and transmitter 100 and exits the download process in step 532.

If it is determined that the minor $T_x$ is greater than the minor $R_x$ in step 506, then in step 526, the transmitter 100 may send notification that a newer version of firmware exists than that available on receiver 114 to users at one or both receiver 114 end and transmitter 100 end. The notification may be sent by methods similar to those described in step 518. The transmitter 100 then records a log of transactions with receiver 114 in one or both receiver 114 and transmitter 100 in step 524 and exits the download process in step 532.

If it is determined in step 504 that the minor $R_x$ is equal to the minor $T_x$, then in step 528, the transmitter 100 may notify users at one or both the receiver 114 and transmitter 100 ends that transmitter 100 has the same version of firmware as stored in receiver 114. The notification may be sent by methods similar to those described in step 518. The transmitter 100 then records a log of transactions with receiver 114 in one or both receiver 114 and transmitter 100 in step 524 and exits the download process in step 532.

In step 530, the transmitter 100 may notify users at one or both receiver 114 and transmitter 100 ends that the firmware stored in receiver 114 may possibly be incompatible with the firmware version loaded in transmitter 100. The notification may be sent by similar methods as described in step 518. The transmitter 100 then records a log of transactions with receiver 114 in one or both receiver 114 and transmitter 100 in step 524 and exits the download process in step 532.

It is to be appreciated that for clarity and ease of illustration, not all steps are illustrated in detail in the flowcharts in FIGS. 4 and 5 because these items are known to those skilled in the relevant art, and are further defined in well known communication standards. Furthermore, it is to be appreciated that similar or substitute steps may be used to implement examples.

Alternate Embodiments of Remote Data Rate Adjustment

In one example the upgrade is performed during a clinician's remote follow-up session with a patient fitted with an IMD 108. A remote upgrade of transmitter 100 firmware is implemented trans-telephonically or via the internet where the receiver 114 communicates with the transmitter 100 at the patient end through telephone lines to accomplish the upgrade during a follow-up session. The upgrade may also be performed via the internet at a later time when the patient can download the upgrade from the internet to the transmitter 100 directly or indirectly through a home computer. In yet another example, the internet upgrade of transmitter 100 firmware can be implemented as an automatic upgrade feature where the receiver 114 or an internet service provider periodically determines the need for an upgrade of transmitter 100 firmware and automatically uploads the firmware upgrade to the transmitter 100 as required. An upgrade may be done by a remote server on the internet where the upgrade firmware is sent through the internet to transmitter 100 which also connects to the internet. The remote server may initiate a download of the necessary firmware to transmitter 100. Alternatively, the remote server may also automatically download the firmware to the patient's home computer from where the patient can then transfer it to transmitter 100. The internet service provider and remote server may be part of communication network 112.

The examples presented above may also ensure proper function of the transmitter 100 in the event the upload or download is incomplete or interrupted as determined in steps 412 and 512. For example the download may be incomplete because of phone line impairments, a corrupt copy of the firmware or a version of hardware that is incompatible with the current firmware update. In the event of an incomplete or corrupt download or incompatible hardware, the transmitter 100 may be able to continue to function on the previous version of firmware. In one example only after the upload or download is verified as being successful with no corruption or hardware incompatibility issues, is the firmware installed in the transmitter by replacing the image of the previous firmware with the image of the new uploaded or downloaded firmware. During the entire upload or download process and installation, transmitter 100 may continue to function normally.

Virtual Receiver

The receiver 114 is typically a custom hardware unit that executes software using its operating system (OS). The physical receiver 114 can be transformed into a "virtual receiver" which is a software executable that may run on a server. The software executable version of physical receiver 114 can perform all the standard receiver 114 functions including those mentioned above. A clinician can perform the same remote patient follow-up session, as with physical receiver 114, from anywhere in the world via the internet by connecting to the server running the virtual receiver version of receiver 114.

Figure 6:
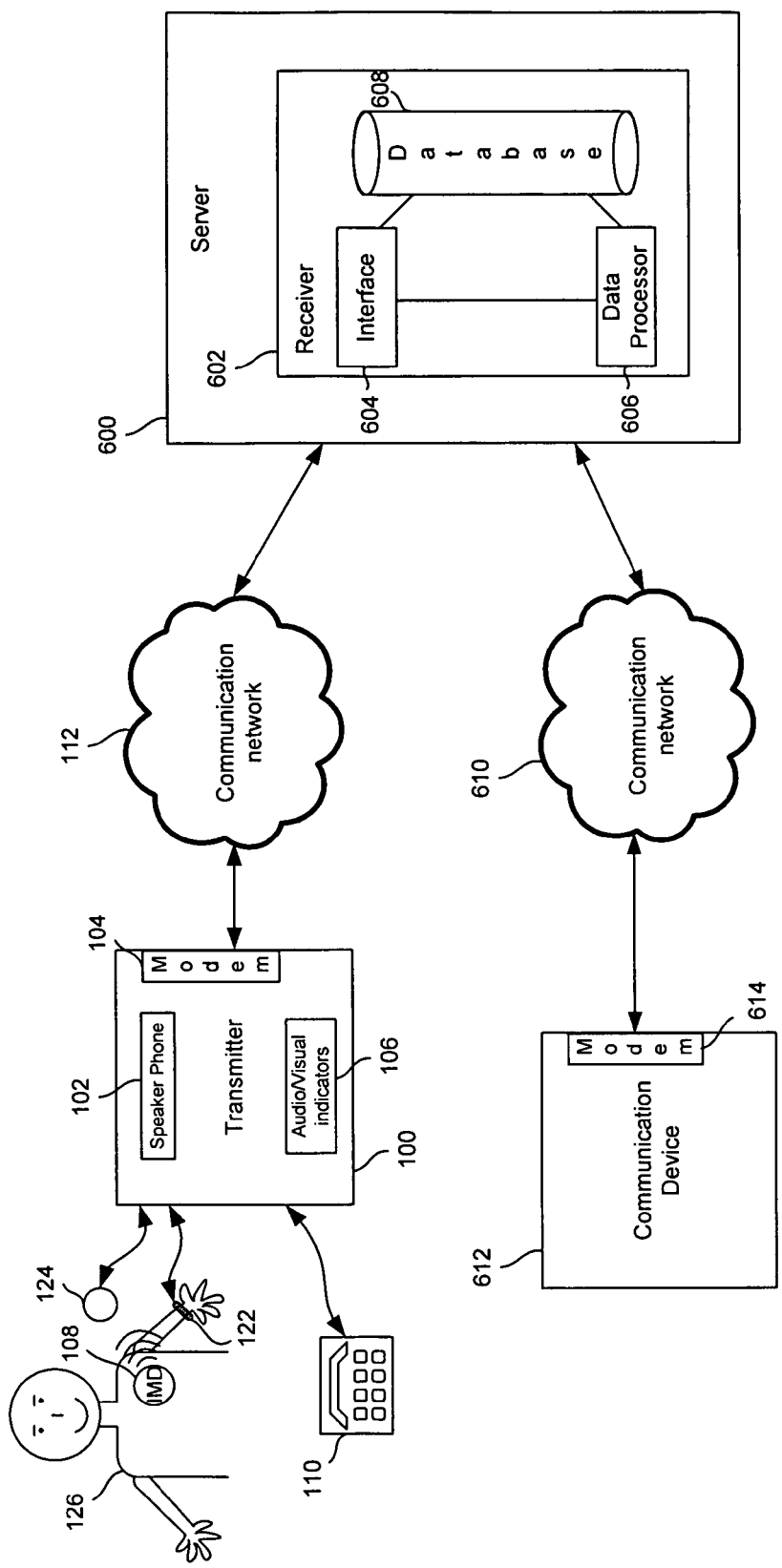
FIG. 6 is a context diagram of a remote monitoring system incorporating a virtual receiver.

FIG. 6 shows an example embodiment of a remote monitoring system using virtual receiver 602. FIG. 6 shows a transmitter 100 with a built in speaker phone 102, modem 104 and audio and visual status indicators 106, a patient 126, an implanted medical device 108, wrist electrodes 122, a wand 124, a transmitter telephone 110, a communication network 112, a server 600, a virtual receiver 602 comprising an interface 604, a data processor 606 and a database 608, communication network 610, a communication device 612 with modem 614.

Functionalities of receiver 114 are transformed into virtual receiver 602 that runs on server 600. Virtual receiver 602 may be software or a combination of hardware and software. Virtual receiver 602 may comprise an interface 604, a data processor 606 and a database 608. Communication device 612 may be used to connect to server 600 through a website via communication network 610. After connecting to virtual receiver 602 via the website, a user may initiate a remote follow-up session with a patient 126. Interface 604 is used to connect to transmitter 100 via communication network 112. Communication devices and protocols inherent to server 600 may be used by interface 604 to connect to transmitter 100. Interface 604 instructs transmitter 100 to interrogate IMD 108 and receive real time and/or stored patient diagnostic data from transmitter 100. Data processor 606 may comprise a GUI, data interpreter and a parsing engine. The GUI may generate one or more web pages or web objects to conduct remote follow-ups via the website. Web pages and web GUI objects may also be generated dynamically by data processor 602 using Active Server Pages (ASP), Java Server Pages (JSP), JAVA applets or third party software such as Macromedia Flash. The data interpreter may convert at least one of the real time patient diagnostic data and stored patient diagnostic data received from transmitter 100 into at least one of a Digital Imaging and Communications in Medicine (DICOM) format, extensible markup language (XML) format and health level 7 (HL7) format. The parsing engine may store in database 608: interpreted data from the data interpreter, archive data from transmitter 100, real time data from transmitter 100 and log reports of transactions between transmitter 100 and virtual receiver 602. It is to be appreciated that virtual receiver 602, interface 604, data processor 606 and database 608 may be implemented in hardware, software, firmware or any combination thereof. For example, functions performed by virtual receiver 602 may be implement on an Application Specific Integrated Circuit (ASIC) or may be software running on a microprocessor.

Figure 7:
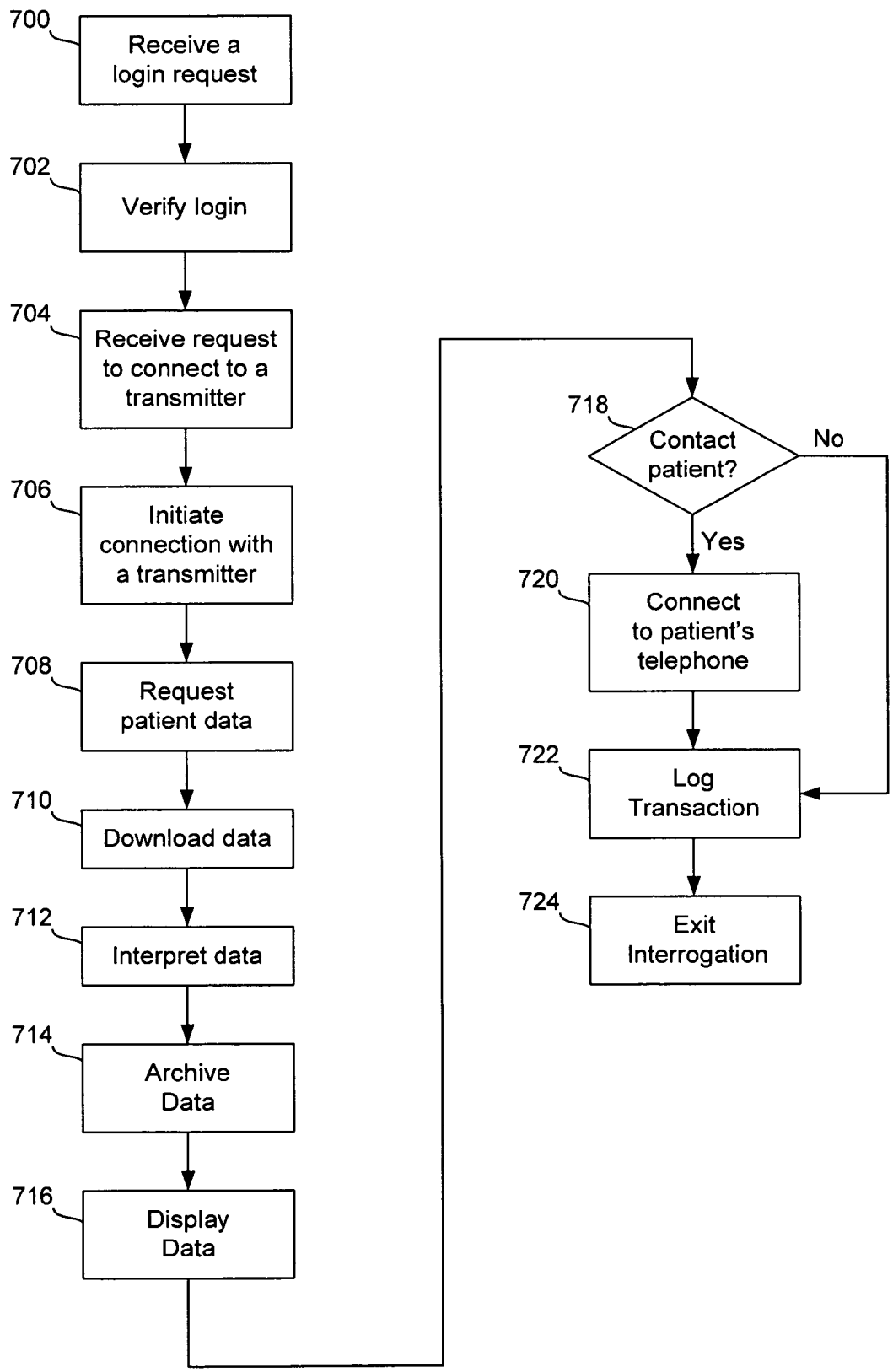
FIG. 7 is an exemplary flowchart of steps that may be performed by a virtual receiver to communicate with a transmitter and with a user via a website.

FIG. 7 is an exemplary flowchart of steps that may be performed by virtual receiver 602. These steps may be performed by receiver 114 hardware, software, firmware or any combination thereof. These steps may also be performed by virtual receiver 602 in conjunction with server 600.

In step 700, virtual receiver 602 receives a login request from a user such as a clinician or physician from communication device 612 through a website generated by server 600 or data processor 606.

In step 702, the login request received in step 600 may be verified by comparing a user entered login and password to information stored in database 608. The virtual receiver 602 may also verify whether the connection is secure by checking the security level of the connection on communication network 610.

In step 704, if a user logged in successfully in step 702, the virtual receiver 602 may receive a request from the clinician to connect to a transmitter 100.

In step 706, the virtual receiver 602 initiates connection with a user specified transmitter 100. The connection may be initiated via interface 604 through communication network 112.

In step 708, the virtual receiver 608 may request patient diagnostic data from transmitter 100 using interface 604 via communication network 112.

In step 710, the virtual receiver 602 may download real time and/or stored patient diagnostic data from transmitter 100 using interface 604 via communication network 112.

In step 712, the virtual receiver 602 may interpret real time and/or stored patient diagnostic data downloaded from transmitter 100 in step 710 using the data interpreter in data processor 602.

In step 714, the virtual receiver 602 may parse the raw real time and/or stored patient diagnostic data downloaded from transmitter 100 in step 710 and/or the interpreted data from step 712 and store it in database 608.

In step 716, the virtual receiver 602 may display the patient diagnostic data on a website using web objects and GUIs that may be generated by the data processor. The user may access the website and view the patient diagnostic data shown using these web objects and GUIs.

In step 718, if the clinician desires to communicate with patient 126, the virtual receiver 602 may query the clinician. The query may be via a web GUI dialog box that requires clinician input.

In step 720, if the clinician decides to initiate a conversation with patient 126 in step 718, then virtual receiver 602 may initiate a call with patient 126 over communication network 112. The patient 126 may communicate via transmitter telephone 110 or speakerphone 102. The clinician may communicate via communication device 612 which may have built in audio capability such as a cellular phone or may be connected to a telephone. The communication networks 112, 610 may be VoIP networks.

In step 722, after the clinician ends the discussion with patient 126 in steps 720 or if the clinician selected to not initiate a conversation with patient 126, the virtual receiver 602 logs an account of the transaction with transmitter 100 and communication device 614 in database 608.

In step 724, the virtual receiver 602 receives an instruction from the clinician via the website to terminate the connection with transmitter 100. The virtual receiver safely disconnects with transmitter 100 using interface 604 and exits the interrogation process.

Alternate Virtual Receiver Embodiments

In one example, communication network 610 is the internet and communication device 612 is a personal computer with a web browser and modem 612. In another example, the communication device 612 may be an internet accessible PDA or cell phone and communication network 610 is a wireless network. The website on server 600 for accessing virtual receiver 602 may provide a GUI for conducting remote patient follow-up and viewing patient diagnostic data. The patient diagnostic data may be processed by data processor 606 and stored in database 608. The virtual receiver 602 may be configured to conduct multiple follow-up sessions simultaneously. The virtual receiver 602 may be implemented in LINUX, UNIX, MAC, WINDOWS or other operating systems.

The parsing engine may be implemented using object oriented languages such as JAVA and C++. The database 602 may store all data received from transmitter 100 in raw or interpreted format. The log reports may detail the transaction history of user logins and system errors. The clinician may also be able to send the user audio/visual alerts via audio/visual indicators 106. If communication device 612 has audio transmission capability then the clinician may also be able to contact patient 126 via transmitter phone 110 or speakerphone 102. At the end of the follow-up session, the clinician may instruct virtual receiver 602 to safely disconnect with transmitter 100 using interface 604. The clinician may then log out of virtual receiver 602 or conduct more follow-up sessions with other patients by initiating connections with other transmitters. Alternatively the clinician may simultaneously conduct multiple follow-up sessions.

In another example, patient 126 may be able to log into virtual receiver 602 using transmitter 100 and/or connect via a website and upload the data from transmitter 100. In one example interface 604 and data processor 606 may be combined into a single unit. This unit may be implemented in hardware, software, firmware or any combination thereof. It is to be appreciated that communication networks 112 and 610 may be the same in some examples.

In the examples presented above, the term "physician" refers to a person who remotely monitors the patient implanted with an IMD or other medical device and conducts a remote follow-up session. The terms physician and clinician are used interchangeably throughout. The terms EGM, ECG, block reading and marker data are merely examples of patient diagnostic data and do not limit the invention in any way. It is to be appreciated that other patient diagnostic data acquired from the patient may be also be transmitted or received.

The communication network 112 may be a public switched telephone network (PSTN), a private branch exchange (PBX), internet, voice over internet protocol (VoIP), broadband network, an optical network, a wide area network, intranet or other wired or wireless communication medium. The receiver 114 and transmitter 100 may be coupled to the communication network 112 via physical, optical, wireless or other media. The modem 104 on the transmitter 100 side may be internal or external to transmitter 100 and modem 128 on the receiver 114 side may be internal or external to receiver 114. Modems 104, 128 are able to communicate via any of the above mentioned communication media in communication network 112.

The present invention, or portions thereof, can be implemented in hardware, firmware, software, and/or combinations thereof.

Figure 8:
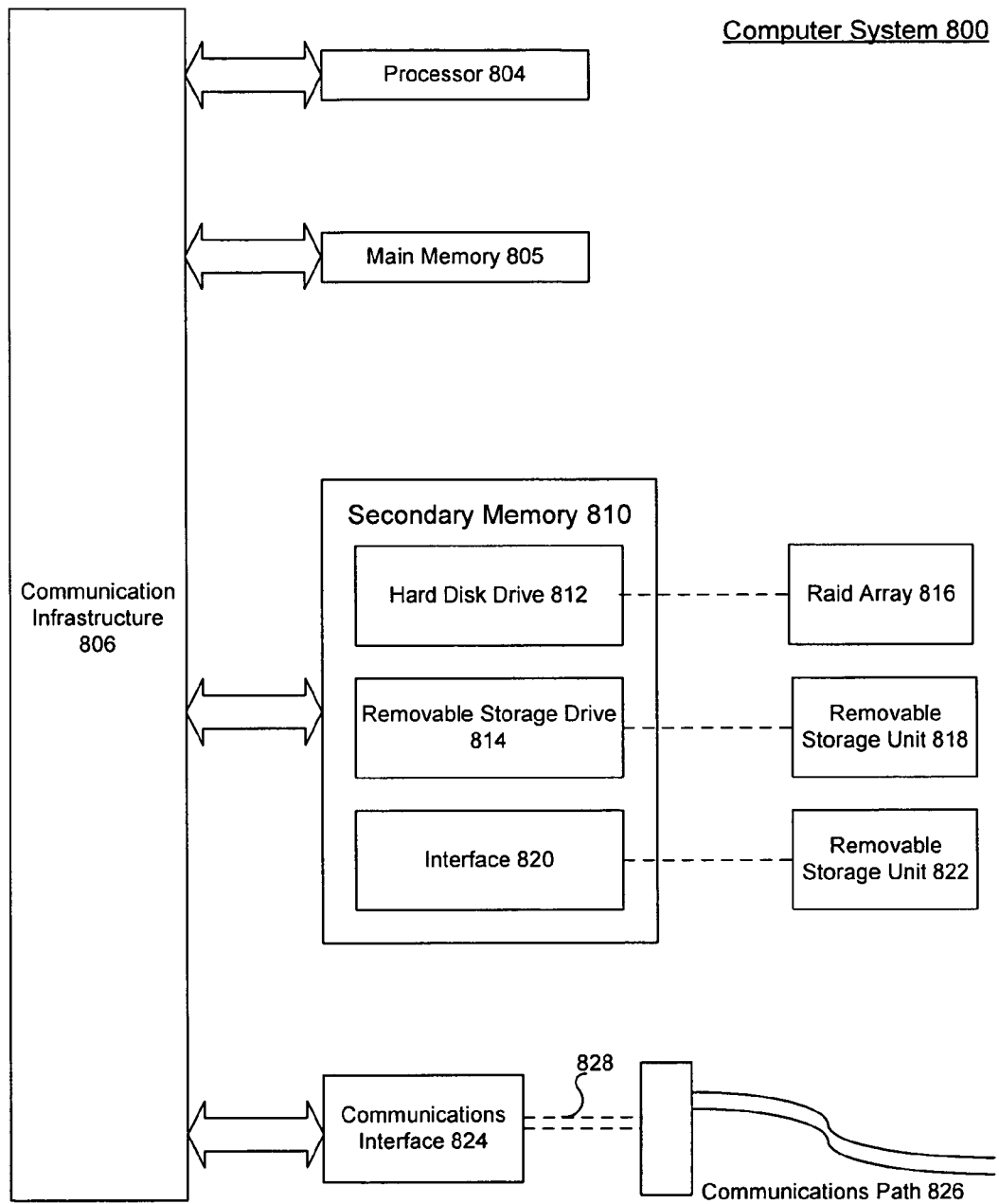
FIG. 8 is a block diagram of a computer system on which the present invention can be implemented.

The following description of a general purpose computer system is provided for completeness. The present invention can be implemented in hardware, or as a combination of software and hardware. Consequently, the invention may be implemented in the environment of a computer system or other processing system. An example of such a computer system 800 is shown in FIG. 8. The computer system 800 includes one or more processors, such as processor 804. Processor 804 can be a special purpose or a general purpose digital signal processor. The processor 804 is connected to a communication infrastructure 806 (for example, a bus or network). Various software implementations are described in terms of this exemplary computer system. After reading this description, it will become apparent to a person skilled in the relevant art how to implement the invention using other computer systems and/or computer architectures.

Computer system 800 also includes a main memory 805, preferably random access memory (RAM), and may also include a secondary memory 810. The secondary memory 810 may include, for example, a hard disk drive 812, and/or a RAID array 816, and/or a removable storage drive 814, representing a floppy disk drive, a magnetic tape drive, an optical disk drive, etc. The removable storage drive 814 reads from and/or writes to a removable storage unit 818 in a well known manner. Removable storage unit 818, represents a floppy disk, magnetic tape, optical disk, etc. As will be appreciated, the removable storage unit 818 includes a computer usable storage medium having stored therein computer software and/or data.

In alternative implementations, secondary memory 810 may include other similar means for allowing computer programs or other instructions to be loaded into computer system 800. Such means may include, for example, a removable storage unit 822 and an interface 820. Examples of such means may include a program cartridge and cartridge interface (such as that found in video game devices), a removable memory chip (such as an EPROM, or PROM) and associated socket, and other removable storage units 822 and interfaces 820 which allow software and data to be transferred from the removable storage unit 822 to computer system 800.

Computer system 800 may also include a communications interface 824. Communications interface 824 allows software and data to be transferred between computer system 800 and external devices. Examples of communications interface 824 may include a modem, a network interface (such as an Ethernet card), a communications port, a PCMCIA slot and card, etc. Software and data transferred via communications interface 824 are in the form of signals 828 which may be electronic, electromagnetic, optical or other signals capable of being received by communications interface 824. These signals 828 are provided to communications interface 824 via a communications path 826. Communications path 826 carries signals 828 and may be implemented using wire or cable, fiber optics, a phone line, a cellular phone link, an RF link and other communications channels.

The terms "computer program medium" and "computer usable medium" are used herein to generally refer to media such as removable storage drive 814, a hard disk installed in hard disk drive 812, and signals 828. These computer program products are means for providing software to computer system 800.

Computer programs (also called computer control logic) are stored in main memory 808 and/or secondary memory 810. Computer programs may also be received via communications interface 824. Such computer programs, when executed, enable the computer system 800 to implement the present invention as discussed herein. In particular, the computer programs, when executed, enable the processor 804 to implement the processes of the present invention. Where the invention is implemented using software, the software may be stored in a computer program product and loaded into computer system 800 using raid array 816, removable storage drive 814, hard drive 812 or communications interface 824.

In other embodiments, features of the invention are implemented primarily in hardware using, for example, hardware components such as Application Specific Integrated Circuits (ASICs) and gate arrays. Implementation of a hardware state machine so as to perform the functions described herein will also be apparent to persons skilled in the relevant art(s).

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

CONCLUSION

While various embodiments of the present invention have been described above, it should be understood that they have been presented by way of example, and not limitation. It will be apparent to persons skilled in the relevant art that various changes in form and detail can be made therein without departing from the spirit and scope of the invention.

The present invention has been described above with the aid of functional building blocks and method steps illustrating the performance of specified functions and relationships thereof. The boundaries of these functional building blocks and method steps have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof. Thus, the breadth and scope of the present invention should not be limited by any of the above-described exemplary embodiments, but should be defined only in accordance with the following claims and their equivalents.

What is claimed is:

1. A method to receive real time data at a receiver at a first location from an implantable medical device at a second location, comprising:
   connecting the receiver at the first location to a transmitter at the second location that is external to the implantable medical device via a communications network;
   determining a data transfer rate of said connection between the receiver and the transmitter over the communications network;
   using the data transfer rate to determine a sampling rate for the real time data received by the transmitter from the implantable medical device;
   sampling real time data from the implantable medical device at the determined sampling rate; and
   receiving the real time data from said transmitter via said communications network.

2. The method of claim 1, further comprising determining at least one diagnostic data type for reception from said transmitter at least in part as a function of said determined data transfer rate.

3. The method of claim 1, further comprising adjusting said sampling rate by sending a packet to said transmitter.

4. The method of claim 1, further comprising instructing said transmitter to combine and transmit a plurality of data packets at least in part as a function of the determined data transfer rate.

5. The method of claim 1, wherein said communications network is at least one of a telephone system, internet, intranet, voice over internet protocol (VoIP), broadband network, an optical network and a wide area network.

6. The method of claim 1, wherein said implantable medical device is an implantable cardioverter defibrillator.

7. The method of claim 1, further comprising receiving stored data from said transmitter via said communications network.

8. A method to receive real time data at a receiver at a first location from an implantable medical device at a second location, comprising:
   connecting a transmitter that is external to the implantable medical device to the receiver via a communications network;
   determining a data transfer rate of said connection between the receiver and the transmitter over the communications network;
   using the data transfer rate to determine a sampling rate for the real time data received by the transmitter from the implantable medical device;
   sampling real time data from the implantable medical device at the determined sampling rate; and
   transmitting the real time data from said transmitter to said receiver via said communications network.

9. The method of claim 8, further comprising determining at least one diagnostic data type for transmission from said transmitter at least in part as a function of said determined data transfer rate.

10. The method of claim 8, further comprising combining a plurality of data packets for transmission from said transmitter at least in part as a function of said determined data transfer rate.

11. The method of claim 8, wherein said communications network is at least one of a telephone system, internet, intranet, voice over internet protocol (VoIP), broadband network, an optical network and a wide area network.

12. The method of claim 8, wherein said implantable medical device is an implantable cardioverter defibrillator.

13. The method of claim 8, further comprising transmitting stored data from said transmitter to said receiver via said communications medium.

14. A method to receive real time data at a receiver at a first location from an implantable medical device at a second location, comprising:
- connecting the receiver to a transmitter via a communications network;
- determining a data transfer rate of said connection between the receiver and the transmitter over the communications network;
- using said data transfer rate to determine a sampling rate between said transmitter and the implantable medical device;
- sampling real time data from the implantable medical device using the transmitter at the determined sampling rate; and
- transmitting the real time data from said transmitter to said receiver.

15. The method of claim 14, wherein said receiver determines at least one diagnostic data type for reception from said transmitter at least in part as a function of the determined data transfer rate.

16. The method of claim 14, further comprising adjusting said sampling rate by sending a packet to from said receiver to said transmitter.

17. The method of claim 14, wherein said transmitter combines a plurality of data packets, for transmission to said receiver, at least in part as a function of the determined data transfer rate.

18. The method of claim 14, wherein said communications network is at least one of a telephone system, internet, intranet, voice over internet protocol (VoIP), a broadband network, an optical network and a wide area network.

19. The method of claim 14, wherein said implantable medical device is an implantable cardioverter defibrillator.

20. The method of claim 14, further comprising transmitting stored data from said transmitter to said receiver via said communications network.

* * * * *